United States Patent [19]

Ozeki et al.

[11] Patent Number: 4,666,915

[45] Date of Patent: May 19, 1987

[54] 2-ANILINO-1,6-DIHYDRO-6-OXO-5-PYRIMIDINE-CARBOXYLIC ACID DERIVATIVES, PROCESS FOR THE PREPARATION THEREOF, AND ANTIALLERGIC AGENT CONTAINING THE SAME

[75] Inventors: Khoji Ozeki; Masahiro Sawada; Isami Kimura, all of Shiga; Mikiko Kataoka, Kusatsu; Makoto Sato; Toshihiro Yamada, both of Moriyama, all of Japan

[73] Assignee: Morishita Pharmaceutical Co. Ltd., Osaka, Japan

[21] Appl. No.: 668,304

[22] Filed: Nov. 5, 1984

[51] Int. Cl.$^4$ .................. C07D 239/47; A61K 31/505

[52] U.S. Cl. .................................... 514/272; 544/321

[58] Field of Search ............................... 544/321, 272

[56] References Cited

U.S. PATENT DOCUMENTS 3,883,653 5/1975 Barth .
3,917,835 12/1975 Barth .
3,957,784 5/1976 Barth .
3,968,213 7/1976 Barth .
4,031,093 6/1977 Juby .

FOREIGN PATENT DOCUMENTS 30177 6/1979 Japan .
376115 5/1964 Switzerland .
1189188 4/1970 United Kingdom .
859716 1/1961 United Kingdom .

OTHER PUBLICATIONS

Juby, et al., *Journal of Medicinal Chemistry,* 22, 1979, pp. 263–269.

Chemical Abstracts, 54, 11038e (1960) Shirakawa and Zasshi.

*Primary Examiner*—Robert Gerstl
*Attorney, Agent, or Firm*—Scully, Scott, Murphy & Presser

[57] ABSTRACT

2-Anilino-1,6-dihydro-6-oxo-5-pyrimidinecarboxylic acid derivatives of the formula:

(I)

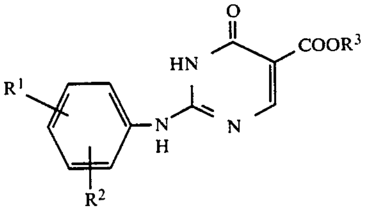

wherein $R^1$ and $R^2$ are the same or different and are each hydrogen, an alkoxy, a tetrahydrofurylalkoxy, an alkyl, an alkoxycarbonyl, a halogen, a dialkylamino, hydroxy, trifluoromethyl, or nitro, and $R^3$ is hydrogen or an alkyl, or a pharmaceutically acceptable salt thereof, which have excellent anti-allergic activities and are useful, particularly for the prophylaxis and treatment of allergic asthma, and processes for the preparation thereof, and anti-allergic agent containing said compounds as an active ingredient.

14 Claims, No Drawings

2-ANILINO-1,6-DIHYDRO-6-OXO-5-PYRIMIDINE-CARBOXYLIC ACID DERIVATIVES, PROCESS FOR THE PREPARATION THEREOF, AND ANTIALLERGIC AGENT CONTAINING THE SAME

The present invention relates to novel 2-anilino-1,6-dihydro-6-oxo-5-pyrimidinecarboxylic acid derivatives, processes for the preparation thereof, and an antiallergic agent containing the same. More particularly, it relates to novel pyrimidinecarboxylic acid derivatives of the formula:

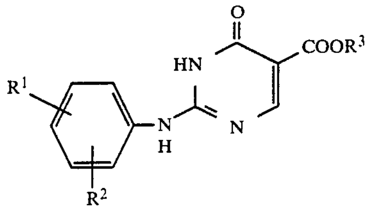

(I)

wherein $R^1$ and $R^2$ are the same or different and are each hydrogen, an alkoxy, a tetrahydrofurylalkoxy, an alkyl, an alkoxycarbonyl, a halogen, a dialkylamino, hydroxy, trifluoromethyl, or nitro, and $R^3$ is hydrogen or an alkyl. The present invention includes also any possible tautomers of the above compounds (I).

In the present specification, the term "alkoxy" denotes a straight or branched chain alkoxy having 1 to 7 carbon atoms, such as methoxy, ethoxy, propoxy, 1-methylethoxy, butoxy, 2-methylpropoxy, pentyloxy, hexyloxy, and heptyloxy. The "tetrahydrofurylalkoxy" denotes a (2,3,4,5-tetrahydrofuran-2-yl)alkoxy having 1 to 4 carbon atoms in the alkoxy moiety, such as (2,3,4,5-tetrahydrofuran-2-yl)methoxy. The "alkyl" denotes a straight or branched chain alkyl having 1 to 4 carbon atoms, such as methyl, ethyl, propyl, n-butyl, sec-butyl, or tert.-butyl. The "alkoxycarbony" denotes an alkoxycarbonyl having 2 to 5 carbon atoms, such as methoxycarbonyl, ethoxycarbonyl, or butoxycarbonyl. The "halogen" denotes fluorine, chlorine, bromine, or iodine. The "dialkylamino" denotes a dialkylamino having 1 to 4 carbon atoms in each alkyl moiety, such as dimethylamino, or diethylamino.

The compounds of the present invention are novel and have excellent antiallergic activities, and are useful as an antiallergic agent. Particularly, the present compouds show sustained antiallergic activities for a long period of time, and hence, are useful for prophylaxis and treatment of allergic asthma.

Barth in U.S. Pat. Nos. 3,883,653, 3,917,835, 3,957,784, and 3,968,213 discloses various 5-carboxypyrimidine derivatives of the formula:

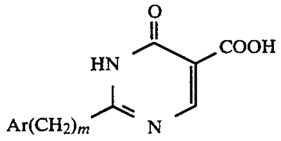

wherein Ar is substituted or unsubstituted aryls (e.g. phenyl unsubstituted or substituted by methyl, methoxy, hydroxy, nitro, halogen, alkanoylamino, or di- or trialkoxyamino, or furyl), m is 0 or 1, or a dimer thereof, and mentions that these compounds have antiallergic activities and are useful particularly for allergic asthma.

However, these known compounds are different from the compounds of the present invention in the point that the pyrimidine ring is bound to the aryl (e.g. phenyl) group directly or via methylene group instead of via imino group as in the present invention.

Juby et al. in U.S. Pat. No. 4,031,093 and in J. of Med. Chem., 1979, Vol. 22, No. 3, pages 263–269 disclose 1,6-dihydro-6-oxo-2-(ortho-substituted phenyl)pyrimidine-5-carboxylic acid derivatives of the formula:

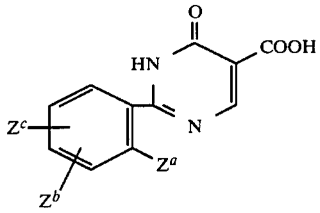

wherein $Z^a$, $Z^b$ and $Z^c$ are each hydrogen or various substituents such as alkoxy, halogen, amino, substituted amino, alkoxycarbonyl, etc., and mention that these compounds have antiallergic activities and are useful as an antiallergic agent, but these compounds are different from the compounds of the present invention in the point that the pyrimidine ring is bound to the benzene ring directly instead of binding via imino group as in the present invention.

The following aminopyrimidine derivatives are disclosed in British Patent No. 1,189,188:

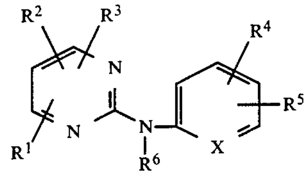

wherein X is nitrogen atom in which case $R^1$, $R^2$, $R^3$, $R^4$ and $R^5$ may be the same or different represent hydrogen, halogen, trifluoromethyl, cyano, alkyl, mercapto, alkylthio, alkylsulphonyl, hydroxy, nitro, carboxy, carbalkoxy, carbamoyl, alkylcarbamoyl, amino, alkylamino, optionally substituted phenylamino, acrylamino, etc.; or x is CH group in which case $R^1$, $R^2$, $R^3$, $R^4$ and $R^5$ are as defined above except that one of $R^1$, $R^2$ and $R^3$ must represent amino, alkylamino, optionally substituted phenylamino or acylamino and if one of $R^1$, $R^2$ and $R^3$ represents an amino group in the 4 position of the pyrimidine ring the remaining two of $R^1$, $R^2$ and $R^3$ may be the same or different and may be any of the radicals or atoms defined above except H and methyl; $R^6$ represents hydrogen or acyl, and this literature discloses that these compounds have antiphlogistic activity. The above general formula is too broadly defined but includes none of the compounds of the present invention. Besides, the pharmacological activity of this literature is different from the antiallergic activities of the present compounds.

Japanese Patent First Publication No. 30177/1979 discloses benzoic acid derivatives of the formula:

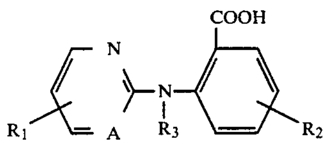

wherein A is =C— or =N—, $R_1$ is (a) hydrogen, lower alkyl, lower alkoxy, condensed benzene ring, or (b) $—CO-R_4$ at 4(or 5)-position, tetrazol-5-yl or cyano, $R_2$ is $—CO-R_4$, tetrazol-5-yl, cyano, or when $R_1$ is the group as defined in (b), $R_2$ may be further hydrogen, lower alkyl, lower alkoxy or condensed benzene ring, $R_3$ is hydrogen or lower acyl, and $R_4$ is hydroxy, amino, hydroxyamino, tetrazol-5-ylamino, or lower alkoxy, and this literature discloses that these compounds have anti-allergic activities and are useful as an anti-allergic agent for the prophylaxis and treatment of allergic diseases, such as asthma, etc. The compounds in this literature are different from the present compounds in the pyrimidine nucleus.

The compounds (I) of the present invention can be prepared by various processes, for example, by the process as shown in the following Reaction Scheme-I.

Reaction Scheme-I

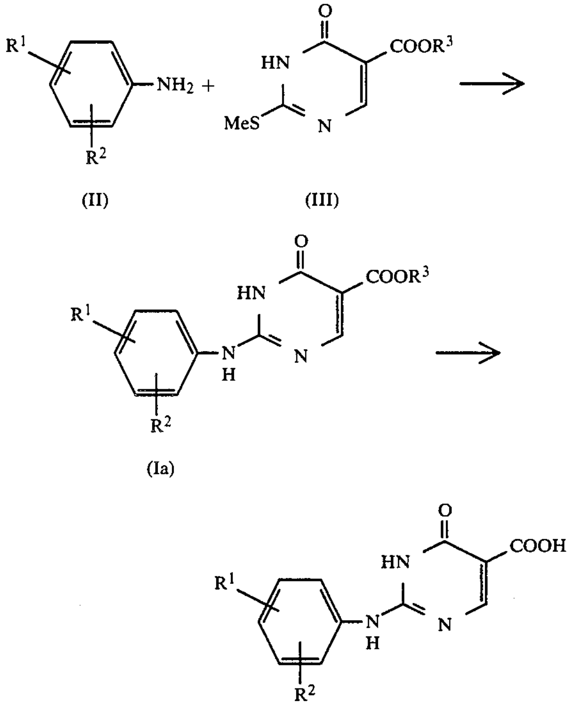

(II) (III)

(Ia)

(Ib)

wherein $R^1$ and $R^2$ are as defined above, $R^3$ is an alkyl, and Me means methyl group.

That is, alkyl 2-(substituted or unsubstituted anilino)-1,6-dihydro-6-oxo-5-pyrimidinecarboxylates of the formula (Ia) are prepared by reacting alkyl 1,6-dihydro-2-methylthio-6-oxo-5-pyrimidinecarboxylate of the formula (III) which is disclosed by C. W. Todd et al. (cf. Journal of the American Chemical Society, 65, 350, 1943) with an aniline derivative of the formula (II). The reaction is easily carried out in a solvent or in the absence of a solvent. The used solvent is not specified unless it participates in the reaction. Suitable examples of the solvent are alcohols (e.g. methanol, ethanol, propanol, butanol, ethylene glycol, or ethylene glycol monomethyl ether), ethers (e.g. dioxane, tetrahydrofuran, ethylene glycol dimethyl ether), pyridine, N,N-dimethylformamide (DMF), dimethyl sulfoxide (DMSO), water, or a mixture of the above organic solvent and water. The reaction temperature is in the range of 50° to 200° C., preferably at a reflux temperature of the solvent. The reaction time is usually in the range of 1 to 72 hours. The amount ratio of the compound (II) to the compound (III) is selected from a wide range; the former is usually used in an amount of 1 to 5 moles, preferably 1 to 1.3 mole, to 1 mole of the latter. In case of using no solvent, the mixture of the compound (II) and the compound (III) is heated at a temperature of 80° to 200° C. for 30 minutes to 20 hours, preferably at a temperature of 100° to 150° C. for several hours, by which the desired compound (Ia) can be obtained in a high yield.

The compound (Ia) thus obtained is hydrolyzed with an alkali in a usual manner to give 2-anilino-1,6-dihydro-6-oxo-5-pyrimidinecarboxylic acid derivative (Ib).

The compound (Ib) thus obtained can be changed into a pharmaceutically acceptable salt thereof, for example, by treating it with an alkali metal hydroxide (e.g. sodium hydroxide, potassium hydroxide, lithium hydroxide), an alkali metal carbonate (e.g. sodium carbonate, sodium hydrogen carbonate, potassium carbonate), or an organic amine (e.g. triethanolamine, trishydroxymethylaminomethane, lysine) to give an alkali metal or organic amine salt thereof.

Alternatively, the compounds (I) of the present invention can be prepared by a process as shown in the following Reaction Scheme-II.

Reaction Scheme-II

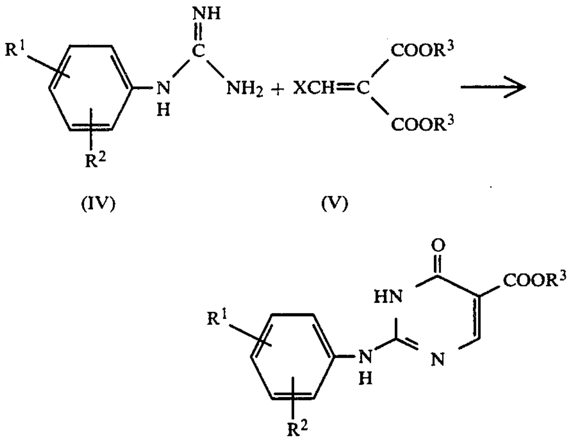

(IV) (V)

(I)

wherein $R^1$ and $R^2$ are as defined above, and X is an alkoxy or a dialkylamino, and $R^3$ is an alkyl.

In the above reaction, the N-phenylguanidine derivative of the formula (IV) prepared by the reaction of an aniline derivative with cyanamide (as is disclosed in John L. Hughes et al., Journal of Medicinal Chemistry, 18, 1077, 1975) is reacted with the alkoxymethylenemalonic acid diester or dialkylaminomethylenemalonic acid diester of the formula (V) (cf. Arthur A. Santilli et al., Journal of Medicinal Chemistry, 7, 68, 1964). The reaction is carried out by heating the reactants in an inert solvent. The solvent is not specified, but suitable examples thereof are alcohols (e.g. ethanol, propanol, butanol, ethylene glycol), ethers (e.g. dioxane, tetrahydrofuran, ethylene glycol dimethyl ether), aromatic hydrocarbons (e.g. benzene, toluene, xylene), pyridine, N,N-dimethylformamide (DMF), dimethyl sulfoxide (DMSO), or the like. The reaction temperature is usually in the range of 80° to 200° C. and the reaction time is usually in the range of 30 minutes to 48 hours. The reaction is advantageously carried out at a reflux temperature of the solvent for several hours.

Besides, when the above reaction is carried out in the presence of a base in a mixed solvent of water and an organic solvent, the reaction proceeds rapidly and can give the desired compounds (I) in a high yield. Suitable examples of the organic solvent to be used in a mixture with water are ethanol, dioxane, tetrahydrofuran or ethylene glycol monomethyl ether, which are used in an appropriate mixed ratio with water, usually in a mixed ratio of equivalent amount or several times larger amount. Suitable examples of the base are potassium carbonate, sodium carbonate, which are used in an amount of 1 to 2 moles to 1 mole of the compound (IV). In the above reaction, the compound (IV) is preferably used in an excess amount, for example, about 1.2 mole to 1 mole of the compound (V). The compound (I) ($R^3$ is an alkyl) thus obtained is optionally hydrolyzed like in Reaction Scheme-I.

The compounds of the present invention, as is disclosed hereinafter, have extremely low toxicity in a toxicity test in mice and have excellent pharmacological activities, i.e. excellent activity in passive cutaneous anaphylaxis (PCA) reaction and also remarkable anti-slow reacting substance of anaphylaxis (SRS-A) action in Magnus method using guinea pig smooth muscle. Accordingly, the compounds of the present invention are useful for the prophylaxis and treatment of asthma, e.g. allergic asthma. Moreover, the compounds are also useful for the prophylaxis and treatment of allergic dermatitis, allergic rhinitis and allergic conjunctivitis.

The compounds of the present invention are administered orally or parenterally in a daily dose of 5 to 2,000 mg, preferably 10 to 500 mg, in adult.

The compounds of the present invention are usually prepared in conventional preparations suitable for oral or parenteral administration, for example, solid preparations such as tablets, capsules, granules, fine granules, or powders, or liquid preparations such as suspensions, solutions, or emulsions. For the oral solid preparations, the compounds of the present invention are admixed with conventional pharmaceutically acceptable carriers or diluents, such as lactose, starches, crystalline cellulose, magnesium stearate, talc, or the like, and the mixture is formed into the desired preparation forms in a usual manner. For parenteral administration, the compounds of the present invention are prepared in the form of an injection by dissolving them in distilled water, wherein glucose, sodium chloride, etc. are usually incorporated in order to make it isotonic. For solution preparation including injection, a solubilizer (e.g. tween 80 and propylene glycol) may optionally be incorporated.

In the preparations, the compounds of the present invention are usually contained in an amount of 1.5 to 700 mg, preferably 3 to 170 mg, per a dosage unit.

The present invention is illustrated by the following Examples and Preparations, but should not be construed to be limited thereto.

EXAMPLE 1

Ethyl 1,6-dihydro-2-methylthio-6-oxo-5-pyrimidinecarboxylate (5 g) and 2-methoxyaniline (3.4 g) are added to DMF (20 ml), and the mixture is refluxed with stirring for 8 hours. After cooling, the precipitate is collected by filtration and recrystallized from DMF to give ethyl 1,6-dihydro-2-(2-methoxyanilino)-6-oxo-5-pyrimidinecarboxylate (5 g). M.p. 217°-219° C.

Elemental analysis for $C_{14}H_{15}N_3O_4$: Calcd. (%): C, 58.12; H, 5.23; N, 14.53. . Found (%): C, 58.17; H, 5.20; N, 14.52.

IR $\nu_{max}^{nujol}$ $cm^{-1}$: 2700-3300 (NH), 1720 (C=O), 1660 (C=O).

NMR (DMSO-$d_6$) δ: 1.24 (3H, t, J=7 Hz, $OCH_2\underline{CH_3}$), 3.86 (3H, s, $OCH_3$), 4.17 (2H, q, J=7 Hz, $OCH_2\overline{CH_3}$), 7.04 (3H, m, Ar—H), 8.16 (1H, d, J-8 Hz, Ar—$\overline{H}$), 8.42 (1H, s, $C_4$—H), 8.40-9.00 (1H, b, NH), 10.00-12.50 (1H, b, NH).

Mass m/e: 289 ($M^+$).

EXAMPLE 2

Ethyl 1,6-dihydro-2-methylthio-6-oxo-5-pyrimidinecarboxylate (8 g) and 2-ethoxyaniline (6.1 g) are added to ethanol (60 ml), and the mixture is refluxed with stirring for 48 hours. After cooling, the precipitate is collected by filtration, washed with ethanol and recrystallized from a mixture of DMF and water to give ethyl 1,6-dihydro-2-(2-ethoxyanilino)-6-oxo-5-pyrimidinecarboxylate (7.5 g). M.p. 220°-221° C.

Elemental analysis for $C_{15}H_{17}N_3O_4$: Calcd. (%): C, 59.39; H, 5.65; N, 13.86. Found (%): C, 59.61; H, 5.56; N, 13.98.

IR $\nu_{max}^{nujol}$ $cm^{-1}$: 3000-3300 (NH), 1720 (C=O), 1600 (C=O).

NMR (DMSO-$d_6$) δ: 1.30 (3H, t, J=7 Hz, $OCH_2CH_3$), 1.36 (3H, t, J=7 Hz, $OCH_2\underline{CH_3}$), 4.20 (2H, q, J=7 Hz, $OCH_2CH_3$), 4.23 (2H, q, J=7 Hz, $O\underline{CH_2}CH_3$), 6.90-7.24 (3H, m, Ar—H), 8.28 (1H, d, J-8 Hz, Ar—H), 8.52 (1H, s, $C_4$—H), 7.00-11.00 (1H, b, 2×NH).

Mass m/e: 303 ($M^+$).

EXAMPLE 3

A mixture of ethyl 1,6-dihydro-2-methylthio-6-oxo-5-pyrimidinecarboxylate (4.2 g) and 2-propoxyaniline (3.5 g) is heated with stirring without a solvent at 120° C. for 1 hour. After cooling, methanol is added to the reaction mixture in order to pulverize the solid, and then the product is collected by filtration and recrystallized from a mixture of DMF and water to give ethyl 1,6-dihydro-2-(2-propoxyanilino)-6-oxo-5-pyrimidinecarboxylate (4.5 g). M.p. 198°-200° C.

Elemental analysis for $C_{16}H_{19}N_3O_4$: Calcd. (%): C, 60.56; H, 6.03; N, 13.24. Found (%): C, 60.73; H, 6.12; N, 13.40.

IR $\nu_{max}^{nujol}$ $cm^{-1}$: 3000-3300 (NH), 1720 (C=O), 1600 (C=O).

NMR (DMSO-$d_6$) δ: 1.00 (3H, t, J=7 Hz, $OCH_2CH_2CH_3$), 1.28 (3H, t, J=7 Hz, $OCH_2\underline{CH_3}$), 1.80 (2H, m, $OCH_2CH_2CH_3$), 4.10 (2H, t, J=7 Hz, $OCH_2CH_2CH_3$), 4.24 (2H, q, J=7 Hz, $O\underline{CH_2}CH_3$), 6.88-7.24 (3H, m, Ar—H), 8.23 (1H, d, J=8 Hz, Ar—H), 8.52 (1H, s, $C_4$—H), 7.80-14.00 (2H, b, 2×NH).

Mass m/e: 317 ($M^+$).

EXAMPLE 4

Ethyl 1,6-dihydro-2-methylthio-6-oxo-5-pyrimidinecarboxylate (15 g) and 2-(1-methylethoxy)aniline (11.5 g) are added to ethanol (100 ml), and the mixture is refluxed with stirring for 17 hours. After cooling, the precipitate is collected by filtration and recrystallized from DMF to give ethyl 1,6-dihydro-2-[2-(1-methylethoxy)anilino]-6-oxo-5-pyrimidinecarboxylate (8.5 g). M.p. 205°-207° C.

Elemental analysis for $C_{16}H_{19}N_3O_4$: Calcd. (%): C, 60.56; H, 6.03; N, 13.24. Found (%): C, 60.73; H, 6.12; N, 13.40.

IR $\nu_{max}^{nujol}$ $cm^{-1}$: 3000-3300 (NH), 1720 (C=O), 1600 (C=O).

NMR (DMSO-$d_6$) δ: 1.34 (6H, d, J=7 Hz, $OCH(C\underline{H}_3)_2$), 1.30 (3H, t, J=7 Hz, $OCH_2CH_3$), 4.26 (2H, q, J=7 Hz, $OC\underline{H}_2CH_3$), 4.73 (1H, m, $OC\underline{H}(CH_3)_2$), 6.86-7.30 (3H, m, Ar—H), 8.32 (1H, d, J-8 Hz, Ar—H), 8.53 (1H, s, $C_4$—H), 8.20-12.30 (2H, b, 2×NH).

Mass m/e: 317 ($M^+$).

EXAMPLE 5

Ethyl 1,6-dihydro-2-methylthio-6-oxo-5-pyrimidinecarboxylate (21.5 g) and 2-butoxyaniline (24 g) are added to pyridine (50 ml), and the mixture is refluxed with stirring for 18 hours. The reaction mixture is concentrated to dryness. The residue is recrystallized from DMF to give ethyl 1,6-dihydro-2-(2-butoxyanilino)-6-oxo-5-pyrimidinecarboxylate (20 g). M.p. 209°-211° C.

Elemental analysis for $C_{17}H_{21}N_3O_4$: Calcd. (%): C, 61.62; H, 6.39; N, 12.68. Found (%): C, 61.80; H, 6.31; N, 12.71.

IR $\nu_{max}^{nujol}$ $cm^{-1}$: 2600-3200 (NH), 1720 (C=O), 1600 (C=O).

NMR (DMSO-$d_6$) δ: 0.94 (3H, t, J=7 Hz, $OCH_2CH_2CH_2C\underline{H}_3$), 1.27 (3H, t, J=7 Hz, $OCH_2C\underline{H}_3$), 1.44 (2H, m, $OCH_2CH_2CHH_2CH_3$), 1.72 (2H, m, $OCH_2C\underline{H}_2CH_2CH_3$), 4.12 (2H, t, J=7 Hz, $OC\underline{H}_2CH_2CH_2CH_3$), 4.29 (2H, q, J=7 Hz, $OC\underline{H}_2CH_3$), 6.90-7.36 (3H, m, Ar—H), 8.16 (1H, d, J-8 Hz, Ar—H), 8.50 (1H, s, $C_4$—H), 6.80-11.50 (2H, b, 2×NH).

Mass m/e: 331 ($M^+$).

EXAMPLE 6

A mixture of ethyl 1,6-dihydro-2-methylthio-6-oxo-5-pyrimidinecarboxylate (50 g) and 2-(2-methylpropoxy)aniline (45 g) is heated with stirring at 120° C. for 2 hours. After cooling, ethanol (300 ml) is added to the reaction mixture and the solid is pulverized, and then the product is collected by filtration and recrystallized from a mixture of DMF and water to give ethyl 1,6-dihydro-2-[2-(2-methylpropoxy)anilino]-6-oxo-5-pyrimidinecarboxylate (57 g). M.p. 188°-190° C.

Elemental analysis for $C_{17}H_{21}N_3O_4$: Calcd. (%): C, 61.62; H, 6.39; N, 12.68. Found (%): C, 61.51; H, 6.32; N, 12.81.

IR $\nu_{max}^{nujol}$ $cm^{-1}$: 3000-3300 (NH), 1720 (C=O), 1600 (C=O).

NMR (DMSO-$d_6$) δ: 1.02 (6H, d, J=7 Hz, $OCH_2CH(C\underline{H}_3)_2$), 1.26 (3H, t, J=7 Hz, $OCH_2C\underline{H}_3$), 2.10 (1H, m, $OCH_2C\underline{H}(CH_3)_2$), 3.81 (2H, d, J=7 Hz, $OC\underline{H}_2CH(CH_3)_2$), 4.17 (2H, q, J=7 Hz, $OC\underline{H}_2CH_3$), 6.80-7.20 (3H, m, Ar—H), 8.07 (1H, d, J=8 Hz, Ar—H), 8.40 (1H, s, $C_4$—H), 8.46 (1H, b, NH), 11.86 (1H, b, NH).

Mass m/e: 331 ($M^+$).

EXAMPLE 7

Ethyl 1,6-dihydro-2-methylthio-6-oxo-5-pyrimidinecarboxylate (10 g) and 3-methoxyaniline (8.5 g) are added to ethanol (150 ml), and the mixture is refluxed with stirring for 17 hours. After cooling, the precipitate is collected by filtration and recrystallized from DMF to give ethyl 1,6-dihydro-2-(3-methoxyanilino)-6-oxo-5-pyrimidinecarboxylate (4.3 g). M.p. 233°-234° C.

Elemental analysis for $C_{14}H_{15}N_3O_4$: Calcd. (%): C, 58.12; H, 5.23; N, 14.53. Found (%): C, 58.33; H, 5.13; N, 14.42.

IR $\nu_{max}^{nujol}$ $cm^{-1}$: 2500-3200 (NH), 1690 (C=O), 1640 (C=O).

NMR (DMSO-$d_6$) δ: 1.28 (3H, t, J=7 Hz, $OCH_2C\underline{H}_3$), 3.80 (3H, s, $OCH_3$), 4.32 (2H, q, J=7 Hz, Ar—H), 7.30 (1H, s, Ar—H), 7.40 (2H, m, Ar—H), 8.63 (1H, s, $C_4$—H), 3.40-12.30 (2H, b, 2×NH).

EXAMPLE 8

Ethyl 1,6-dihydro-2-methylthio-6-oxo-5-pyrimidinecarboxylate (10 g) and 4-ethoxyaniline (14.3 g) are added to ethanol (150 ml), and the mixture is refluxed with stirring for 17 hours. After cooling, the precipitate is collected by filtration and recrystallized from DMF to give ethyl 1,6-dihydro-2-(4-ethoxyanilino)-6-oxo-5-pyrimidinecarboxylate (10 g). M.p. 263°-265° C.

Elemental analysis for $C_{15}H_{17}N_3O_4$: Calcd. (%): C, 59.39; H, 5.65; N, 13.86. Found (%): C, 59.02; H, 5.52; N, 13.88.

IR $\nu_{max}^{nujol}$ $cm^{-1}$: 2500-3320 (NH), 1715 (C=O), 1645 (C=O).

NMR (DMSO-$d_6$) δ: 1.27 (3H, t, J=7 Hz, $OCH_2C\underline{H}_3$), 1.34 (3H, t, J=7 Hz, $OCH_2CH_3$), 4.07 (2H, q, J=7 Hz, $OC\underline{H}_2CH_3$), 4.24 (2H, q, J=7 Hz, $OC\underline{H}_2CH_3$), 6.95 (2H, d, J=8 Hz, Ar—H), 7.48 (2H, d, J=8 Hz, Ar—H), 8.47 (1H, s, $C_4$—H), 7.40-12.00 (2H, b, 2×NH).

Mass m/e: 303 ($M^+$).

EXAMPLE 9

Ethyl 1,6-dihydro-2-methylthio-6-oxo-5-pyrimidinecarboxylate (10 g) and 2,5-dimethoxyaniline (8.6 g) are added to ethanol (200 ml), and the mixture is refluxed with stirring for 17 hours. After cooling, the precipitate is collected by filtration and recrystallized from a mixture of DMF and water to give ethyl 1,6-dihydro-2-(2,5-dimethoxyanilino)-6-oxo-5-pyrimidinecarboxylate (8.8 g). M.p. 221°-223° C.

Elemental analysis for $C_{15}H_{17}N_3O_5$: Calcd. (%): C, 56.42; H, 5.63; N, 13.16. Found (%): C, 56.21; H, 5.21; N, 13.05.

IR $\nu_{max}^{nujol}$ $cm^{-1}$: 2600-3200 (NH), 1720 (C=O), 1605 (C=O). NMR (DMSO-$d_6$) δ: 1.27 (3H, t, J=8 Hz, $OCH_2C\underline{H}_3$), 3.73 (3H, s, $OCH_3$), 3.84 (3H, s, $OCH_3$), 4.22 (2H, q, J=8 Hz, $OC\underline{H}_2CH_3$), 6.66 (1H, dd, $J_1$=8 Hz, $J_2$=4 Hz, Ar—H), 7.00 (1H, d, J=8 Hz, Ar—H), 8.48(1H, s, $C_4$—H), 7.00-11.86 (2H, b, 2×NH).

Mass m/e: 319 ($M^+$).

In the same manne as described in Example 9, corresponding aniline derivatives are reacted with ethyl 1,6-dihydro-2-methylthio-6-oxo-5-pyrimidinecarboxylate to give the compounds of Examples 10 to 32. The compounds thus obtained and analytical data thereof are shown in Table 1.

TABLE 1

Compounds

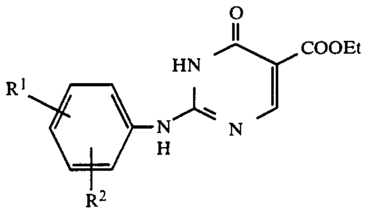

| Ex. No. | $R^1$ (binding position) | $R^2$ (binding position) | M.p. (°C.) | IR $\nu_{max}^{nujol}$ $cm^{-1}$ (c = 0) | Mass m/e ($M^+$) | NMR ($DMSO-d_6$) $\delta(C_4-H)$ |
|---|---|---|---|---|---|---|
| 10 | H | $O(CH_2)_4CH_3$ (2-position) | 170–172 | 1600, 1720 | 345 | 8.40 |
| 11 | H | $O(CH_2)_2CH(CH_3)_2$ (2-position) | 178–180 | 1605, 1715 | 345 | 8.47 |
| 12 | H | $O(CH_2)_5CH_3$ (2-position) | 168–170 | 1600, 1720 | 359 | 8.48 |
| 13 | H | $O(CH_2)_6CH_3$ (2-position) | 150–152 | 1600, 1715 | 373 | 8.48 |
| 14 | H | 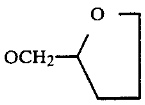 (2-position) | 165–167 | 1600, 1715 | 359 | 8.46 |
| 15 | H | $O(CH_2)_2CH_3$ (3-position) | 184–186 | 1640, 1700 | 317 | 8.43 |
| 16 | H | $O(CH_2)_3CH_3$ (3-position) | 181–183 | 1650, 1695 | 331 | 8.43 |
| 17 | H | $O(CH_2)_4CH_3$ (3-position) | 183–185 | 1645, 1695 | 345 | 8.45 |
| 18 | H | $O(CH_2)_2CH_3$ (4-position) | 258–260 | 1645, 1715 | 317 | 8.47 |
| 19 | H | $OCH(CH_3)_2$ (4-position) | 248–250 | 1640, 1680 | 317 | 8.47 |
| 20 | H | $O(CH_2)_3CH_3$ (4-position) | 238–240 | 1640, 1680 | 331 | 8.45 |
| 21 | H | $OCH_2CH(CH_3)_2$ (4-position) | 251–253 | 1640, 1680 | 331 | 8.45 |
| 22 | H | $O(CH_2)_4CH_3$ (4-position) | 242–244 | 1640, 1690 | 345 | 8.46 |
| 23 | H | $O(CH_2)_2CH(CH_3)_2$ (4-position) | 231–232 | 1640, 1680 | 345 | 8.48 |
| 24 | H | $O(CH_2)_5CH_3$ (4-position) | 229–231 | 1640, 1680 | 359 | 8.48 |
| 25 | $OCH_2CH_3$ (2-position) | $OCH_2CH_3$ (5-position) | 227–229 | 1600, 1720 | 347 | 8.59 |
| 26 | $O(CH_2)_2CH_3$ (2-position) | $O(CH_2)_2CH_3$ (5-position) | 180–182 | 1610, 1720 | 375 | 8.08 |
| 27 | $O(CH_2)_3CH_3$ (2-position) | $O(CH_2)_3CH_3$ (5-position) | 160–162 | 1610, 1720 | 403 | 8.55 |
| 28 | $OCH(CH_3)_2$ (2-position) | $OCH(CH_3)_2$ (5-position) | 208–210 | 1615, 1720 | 375 | 8.55 |
| 29 | $OCH_2CH(CH_3)_2$ (2-position) | $OCH_2CH(CH_3)_2$ (5-position) | 166–168 | 1615, 1720 | 403 | 8.53 |
| 30 | $OCH_2CH_3$ (3-position) | $OCH_2CH_3$ (4-position) | 220–222 | 1615, 1720 | 347 | 8.53 |
| 31 | $O(CH_2)_2CH_3$ (3-position) | $O(CH_2)_2CH_3$ (4-position) | 145–147 | 1625, 1720 | 375 | 8.52 |
| 32 | $O(CH_2)_3CH_3$ (3-position) | $O(CH_2)_3CH_3$ (4-position) | 145–147 | 1620, 1720 | 403 | 8.56 |

EXAMPLE 33

Ethyl 1,6-dihydro-2-methylthio-6-oxo-5pyrimidinecarboxylate (10 g) and 2,5-dimethylaniline (8.5 g) are added to ethanol (150 ml), and the mixture is refluxed with stirring for 17 hours. After cooling, the precipitate is collected by filtration and recrystallized from DMF to give ethyl 1,6-dihydro-6-oxo-2-(2,5-dimethylanilino)-5-pyrimidinecarboxylate (6.1 g). M.p. 252°-254° C.

Elemental analysis for $C_{15}H_{17}N_3O_3$: Calcd. (%): C, 62.70; H, 5.96; N, 14.63. Found (%): C, 62.49; H, 5.99; N, 14.71.

IR $\nu_{max}^{nujol}$ $cm^{-1}$: 2500-3200 (NH), 1690 (C═O), 1640 (C═O).

NMR ($DMSO-d_6$) $\delta$: 1.25 (3H, t, J=7 Hz, $OCH_2C\underline{H}_3$),2.20 (3H, s, $CH_3$), 2.30 (3H, s, $CH_3$), 4.23

(2H, q, J=7 Hz, $OCH_2CH_3$), 7.00 (1H, d, J=8 Hz, Ar—H), 7.12 (1H, d, J=8 Hz, Ar—H), 7.40 (1H, s, Ar—H), 8.40 (1H, s, $C_4$—H), 8.50-11.60 (2H, b, 2×NH).

Mass m/e: 287 (M+).

EXAMPLE 34

Ethyl 1,6-dihydro-2-methylthio-6-oxo-5-pyrimidinecarboxylate (50 g) and 3-aminobenzotrifluoride (45.2 g) are added to ethanol (300 ml), and the mixture is refluxed with stirring for 17 hours. After cooling, the precipitate is collected by filtration and recrystallized from a mixture of DMF and water to give ethyl 1,6-dihydro-6-oxo-2-(3-trifluoromethylanilino)-5-pyrimidinecarboxylate (34.4 g). M.p. 229°-230° C.

Elemental analysis for $C_{14}H_{12}N_3O_3F_3$: Calcd. (%): C, 51.38; H, 3.67; N, 12.84. Found (%): C, 51.52; H, 3.76; N, 12.67.

IR $\nu_{max}^{nujol}$ $cm^{-1}$: 2500-3400 (NH), 1720 (C=O), 1605 (C=O).

NMR (DMSO-$d_6$) δ: 1.30 (3H, t, J=7 Hz, $OCH_2CH_3$), 4.26 (2H, q, J=7 Hz, $OCH_2CH_3$), 7.40-8.20 (4H, m, Ar—H), 8.60 (1H, s, $C_4$—H), 9.00-12.50 (2H, b, 2×NH).

Mass m/e: 327 (M+).

EXAMPLE 35

Ethyl 1,6-dihydro-2-methylthio-6-oxo-5-pyrimidinecarboxylate (20 g) and 4-(N,N-dimethylamino)aniline (19 g) are added to ethanol (200 ml), and the mixture is refluxed with stirring for 19 hours. After cooling, the precipitate is collected by filtration and recrystallized from a mixture of DMF and water to give ethyl 1,6-dihydro-2-[4-(N,N-dimethylamino)anilino]-6-oxo-5-pyrimidinecarboxylate (15.7 g).

M.p. 246°-248° C.

Elemental analysis for $C_{15}H_{18}N_4O_3$: Calcd. (%): C, 59.59; H, 6.00; N, 18.53. Found (%): C, 59.46; H, 5.96; N, 18.69.

IR $\nu_{max}^{nujol}$ $cm^{-1}$: 2400-3300 (NH), 1730 (C=O), 1640 (C=O).

NMR (DMSO-$d_6$) δ: 1.25 (3H, t, J=7 Hz, $OCH_2CH_3$), 2.88 (6H, s, $N(CH_3)_2$), 4.22 (2H, q, J=7 Hz, $OCH_2CH_3$), 6.74 (2H, d, J=8 Hz, Ar—H), 7.46 (2H, d, J=8 Hz, Ar—H), 8.45 (1H, s, $C_4$—H), 8.40-11.60 (2H, b, 2×NH).

Mass m/e: 302 (M+).

EXAMPLE 36

Ethyl 1,6-dihydro-2-methylthio-6-oxo-5-pyrimidinecarboxylate (40 g) and 2-aminophenol (22.4 g) are added to DMF (80 ml), and the mixture is heated with stirring at 110° C. for 18 hour. After cooling, the precipitate is collected by filtration and recrystallized from DMF to give ethyl 1,6-dihydro-2-(2-hydroxyanilino)-6-oxo-5-pyrimidinecarboxylate (29 g). M.p. 289°-291° C.

Elemental analysis for $C_{13}H_{13}N_3O_4$: Calcd. (%): C, 56.72; H, 4.76; N, 15.27. Found (%): C, 56.60; H, 4.74; N, 15.40.

IR $\nu_{max}^{nujol}$ $cm^{-1}$: 2300-3400 (NH, OH), 1685 (C=O), 1650 (C=O).

NMR (DMSO-$d_6$) δ: 1.26 (3H, t, J=7 Hz, $OCH_2CH_3$), 4.24 (2H, q, J=7 Hz, $OCH_2CH_3$), 6.80-7.10 (3H, m, Ar—H), 8.10 (1H, d, J=8 Hz, Ar—H), 8.50 (1H, s, $C_4$—H), 7.00-14.00 (3H, b, 2×NH, OH).

Mass m/e: 275 (M+).

EXAMPLE 37

Ethyl 1,6-dihydro-2-methylthio-6-oxo-5-pyrimidinecarboxylate (20 g) and 2-fluoroaniline (15.6 g) are added to ethanol (200 ml), and the mixture is refluxed with stirring for 24 hours. After cooling, the precipitate is collected by filtration and recrystallized from DMF to give ethyl 1,6-dihydro-2-(2-fluoroanilino)-6-oxo-5-pyrimidinecarboxylate (4.5 g). M.p. 250°-252° C.

Elemental analysis for $C_{13}H_{12}N_3O_3F$: Calcd. (%): C, 56.12; H, 4.33; N, 15.16. Found (%): C, 55.96; H, 4.28; N, 15.30.

IR $\nu_{max}^{nujol}$ $cm^{-1}$: 2500-3300 (NH), 1695 (C=O), 1620 (C=O).

NMR (DMSO-$d_6$) δ: 1.24 (3H, t, J=7 Hz, $OCH_2CH_3$), 4.23 (2H, q, J=7 Hz, $OCH_2CH_3$), 7.12-7.50 (3H, m, Ar—H), 8.50 (1H, s, $C_4$—H), 8.00-11.00 (2H, b, 2×NH).

Mass m/e: 277 (M+).

EXAMPLE 38

Ethyl 1,6-dihydro-2-methylthio-6-oxo-5-pyrimidinecarboxylate (10 g) and butyl -4-aminobenzoate (10.8 g) are added to ethanol (100 ml), and the mixture is refluxed with stirring for 48 hours. After cooling, the precipitate is collected by filtration and recrystallized from a mixture of DMF and water to give ethyl 1,6-dihydro-2-(4-butoxycarbonylanilino)-6-oxo-5-pyrimidinecarboxylate (7.0 g). M.p. 281°-283° C.

Elemental analysis for $C_{18}H_{21}N_3O_5$: Calcd. (%): C, 60.16; H, 5.89; N, 11.69. Found (%): C, 59.81; H, 5.87; N, 11.46.

IR $\nu_{max}^{nujol}$ $cm^{-1}$: 2500-3300 (NH), 1725 (C=O), 1715 (C=O), 1650 (C=O).

NMR (DMSO-$d_6$) δ: 0.98 (3H, t, J=7 Hz, $OCH_2CH_2CH_2CH_3$), 1.31 (3H, t, J=7 Hz, $OCH_2CH_3$), 1.50 (2H, m, $OCH_2CH_2CH_2CH_3$), 1.70 (2H, m, $OCH_2CH_2CH_2CH_3$), 4.31 (2H, q, J=7 Hz, $OCH_2CH_2CH_2CH_3$), 4.33 (2H, q, J=7 Hz, $OCH_2CH_3$), 7.80-8.20 (4H, m, Ar—H), 8.64 (1H, s, $C_4$—H), 8.40-11.60 (2H, b, 2×NH).

Mass m/e: 359 (M+).

EXAMPLE 39

A mixture of ethyl 1,6-dihydro-2-methylthio-6-oxo-5-pyimidinecarboxylate (10 g) and 3-nitroaniline (7.7 g) is heated with stirring without solvent at 120° C. for 1 hour. After cooling, methanol (50 ml) is added to the reaction mixture to pulverize solid. The resulting product is collected by filtration and recrystallized from DMF to give ethyl 1,6-dihydro-2-(3-nitroanilino)-6-oxo-5-pyrimidinecarboxylate (8.5 g). M.p. 226°-228° C.

Elemental analysis for $C_{13}H_{12}N_4O_5$: Calcd. (%): C, 51.32; H, 3.95; N, 18.42. Found (%): C, 51.15; H, 3.92; N, 18.30.

IR $\nu_{max}^{nujol}$ $cm^{-1}$: 2400-3340 (NH), 1730 (C=O), 1600 (C=O).

NMR (DMSO-$d_6$) δ: 1.32 (3H, t, J=7 Hz, $OCH_2CH_3$), 4.30 (2H, q, J=7 Hz, $OCH_2CH_3$), 7.58 (1H, t, J=7 Hz, Ar—H), 7.80-8.12 (2H, m, Ar—H), 8.55 (1H, s, $C_4$—H), 8.60 (1H, m, Ar—H), 1.40-9.00 (2H, b, 2×NH).

Mass m/e: 304 (M+).

In the same manner as described in Examples 38 and 39, corresponding aniline derivatives are reacted with ethyl 1,6-dihydro-2-methylthio-6-oxo-5-pyrimidinecarboxylate to give the compounds of Examples 40 to 46. The compounds thus obtained and analytical data thereof are shown in Table 2.

TABLE 2

Compounds

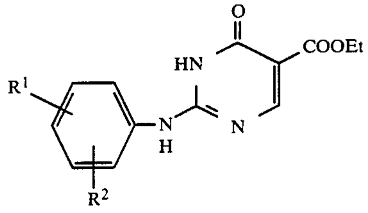

| Ex. No. | $R^1$ (binding position) | $R^2$ (binding position) | M.p. (°C.) | IR $\nu_{max}^{nujol}$ cm$^{-1}$ (c = 0) | Mass m/e ($M^+$) | NMR (DMSO-$d_6$) δ($C_4$—H) |
|---|---|---|---|---|---|---|
| 40 | H | $(CH_2)_3CH_3$ (4-position) | 248–251 | 1640, 1690 | 315 | 8.47 |
| 41 | H | $CH_2CH_3$ (4-position) | 265–267 | 1650, 1685 | 287 | 8.44 |
| 42 | H | F (3-position) | 290–293 | 1640, 1690 | 277 | 8.64 |
| 43 | H | F (4-position) | 300 | 1640, 1690 | 277 | 8.64 |
| 44 | H | Br (2-position) | 300 | 1640, 1695 | 337 | 8.64 |
| 45 | H | Cl (3-position) | 270–272 | 1650, 1725 | 293 | 8.60 |
| 46 | H | COOEt (3-position) | 221–223 | 1675, 1715, 1730 | 331 | 8.60 |

EXAMPLE 47

Ethyl 1,6-dihydro-2-(2-methoxyanilino)-6-oxo-5-pyrimidinecarboxylate (10 g) and sodium hydroxide (4 g) are added to water (100 ml), and the mixture is refluxed with stirring for 1 hour. After cooling, the reaction mixture is acidified with acetic acid, and the precipitate is collected by filtration and recrystallized from DMF to give 1,6-dihydro-2-(2-methoxyanilino)-6-oxo-5-pyrimidinecarboxylic acid (7 g). M.p. 251°–253° C.

Elemental analysis for $C_{12}H_{11}N_3O_4$: Calcd. (%): C, 55.17; H, 4.24; N, 16.09. Found (%): C, 55.20; H, 4.53; N, 16.03.

IR $\nu_{max}^{nujol}$cm$^{-1}$2200–3400 (NH, OH), 1720 (C═O), 1660 (C═O).

NMR (DMSO-$d_6$) δ: 3.94 (3H, s, $OCH_3$), 6.92–7.32 (3H, m, Ar—H), 8.16 (1H, d, J=8 Hz, Ar—H), 8.58 (1H, s, $C_4$—H), 8.00–13.80 (3H, b, 2×NH, OH).

Mass m/e: 261 ($M^+$).

EXAMPLE 48

Ethyl 1,6-dihydro-2-(2-ethoxyanilino)-6-oxo-5-pyrimidinecarboxylate (3.4 g) and sodium hydroxide (1 g) are added to water (50 ml), and the mixture is refluxed with stirring for 1 hour. After cooling, the reaction mixture is acidified with acetic acid, and the resulting solid is collected by filtration and recrystallized from DMF. The precipitate thus obtained is added to water (50 ml), and the mixture is refluxed with stirring for 1 hour. After cooling, the resulting product is collected by filtration and dried at 80° C. under reduced pressure to give 1,6-dihydro-2-(2-ethoxyanilino)-6-oxo-5-pyrimidinecarboxylic acid (2 g). M.p. 226°–228° C.

Elemental analysis for $C_{13}H_{13}N_3O_4$: Calcd. (%): C, 56.72; H, 4.76; N, 15.72. Found (%): C, 56.68; H, 4.66; N, 15.30.

IR $\nu_{max}^{nujol}$ cm$^{-1}$: 2400–3300 (NH, OH), 1720 (C═O), 1630 (C═O).

NMR (DMSO-$d_6$) δ: 1.38 (3H, t, J=7 L Hz, $OCH_2CH_3$), 4.16 (2H, q, J=7 Hz, $OCH_2CH_3$), 6.88–7.40 (3H, m, Ar—H), 8.15 (1H, d, J=8 Hz, Ar—H), 8.56 (1H, s, $C_4$—H), 8.40–14.00 (3H, b, 2×NH, OH).

Mass m/e: 275 ($M^+$).

EXAMPLE 49

Ethyl 1,6-dihydro-2-(2-propoxyanilino)-6-oxo-5-pyrimidinecarboxylate (8 g) and sodium hydroxide (3 g) are added to water (100 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (100 ml), and the mixture is refluxed with stirring for 1 hour. After cooling, the product is collected by filtration and dried at 80° C. under reduced pressure to give 1,6-dihydro-2-(2-propoxyanilino)-6-oxo-5-pyrimidinecarboxylic acid (4.5 g). M.p. 202°–204° C.

Elemental analysis for $C_{14}H_{15}N_3O_4$: Calcd. (%): C, 58.13; H, 5.23; N, 14.53. Found (%): C, 58.04; H, 5.16; N, 14.42.

IR $\nu_{max}^{nujol}$ cm$^{-1}$: 2200–3200 (NH, OH), 1720 (C═O), 1640 (C═O).

NMR (DMSO-$d_6$) δ: 1.00 (3H, t, J=7 Hz, $OCH_2CH_2CH_3$), 1.32 (2H, m, $OCH_2CHCH_2CH_3$), 4.07 (2H, t, J=7 Hz, $OCH_2CH_2CH_3$), 6.90–7.34 (3H, m, Ar—H), 8.14 (1H, d, J=8 Hz, Ar—H), 8.59 (1H, s, $C_4$—H), 6.80–13.00 (3H, b, 2×NH, OH).

Mass m/e: 289 ($M^+$).

EXAMPLE 50

Ethyl 1,6-dihydro-2-[2-(1-methylethoxy)anilino]-6-oxo-5-pyrimidinecarboxylate (7.5 g) and sodium hydroxide (3 g) are added to water (100 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (80 ml), and the mixture is refluxed with stirring for 1 hour. After cooling, the resulting product is collected by filtration and dried at 80° C. under reduced pressure to give 1,6-dihydro-2-[b 2-(1-methylethoxy)anilino]-6-oxo-5-pyrimidinecarboxylic acid (6.7 g). M.p. 202°–204° C.

Elemental analysis for $C_{14}H_{15}N_3O_4$: Calcd. (%): C, 58.13; H, 5.23; N, 14.53. Found (%): C, 57.96; H, 5.24; N, 14.34.

IR $\nu_{max}^{nujol}$ cm$^{-1}$: 2400–3300 (NH, OH),1725 (C═O), 1650 (C═O).

NMR (DMSO-$d_6$) δ: 1.30 (6H, d, J=7 Hz, $OCH(CH_3)_2$), 4.86 (1H, m, $OCH(CH_3)_2$), 6.88–7.28 (3H, m, Ar—H), 8.20 (1H, d, J=8 Hz, Ar—H), 8.60 (1H, s, $C_4$—H), 4.00–12.00 (3H, b, 2×NH, OH).

Mass m/e: 289 ($M^+$).

EXAMPLE 51

Ethyl 1,6-dihydro-2-(2-butoxyanilino)-6-oxo-5-pyrimidinecarboxylate (12 g) and sodium hydroxide (3 g) are added to water (150 ml), and the mixture is refluxed with stirring for 1 hour. After cooling, the reaction mixture is acidified with acetic acid, and the resulting solid is collected by filtration and recrystallized from DMF. The precipitate thus obtained is collected by filtration and added to water (100 ml), and the mixture is refluxed with stirring for 1 hour. After cooling, the resulting product is collected by filtration and dried at 80° C. under reduced pressure to give 1,6-dihydro-2-(2-butoxyanilino)-6-oxo-5-pyrimidinecarboxylic acid (8 g). M.p. 212°-214° C.

Elemental analysis for $C_{15}H_{17}N_3O_4$: Calcd. (%): C, 59.39; H, 5.65; N, 13.86. Found (%): C, 59.25; H, 5.84; N, 14.00.

IR $\nu_{max}^{nujol}$ $cm^{-1}$: 2400-3300 (NH, OH), 1720 (C=O), 1630 (C=O).

NMR (DMSO-$d_6$) δ: 0.92 (3H, t, J=7 Hz, $OCH_2CH_2CH_2C\underline{H}_3$), 1.44 (2H, m, $OCH_2CH_2C\underline{H}_2CH_3$), 1.73 (2H, m, $OCH_2\underline{CH_2}CH_2CH_3$), 4.10 (3H, t, J=7 Hz, $OC\underline{H}_2CH_2CH_2CH_3$), 6.88-7.36 (3H, m, Ar—H), 8.59 (1H, s, $C_5$—H), 6.80-12.00 (3H, b, 2×NH, OH).

Mass m/e: 303 (M+).

EXAMPLE 52

Ethyl 1,6-dihydro-2-[2-(2-methylpropoxy)anilino]-6-oxo-5-pyrimidinecarboxylate (7.5 g) and sodium hydroxide (3 g) are added to water (100 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (100 ml), and the mixture is refluxed with stirring for 1 hour. After cooling, the resulting product is collected by filtration and dried at 80° C. under reduced pressure to give 1,6-dihydro-2-[2-(2-methylpropoxy)anilino]-6-oxo-5-pyrimidinecarboxylic acid (4.3 g). M.p. 213°-215° C.

Elemental analysis for $C_{15}H_{17}N_3O_4$: Calcd. (%): C, 59.39; H, 5.65; N, 13.86. Found (%): C, 58.99; H, 5.68; N, 13.48.

IR $\nu_{max}^{nujol}$ $cm^{-1}$: 2400-3200 (NH, OH), 1720 (C=O), 1630 (C=O).

NMR (DMSO-$d_6$) δ: 0.98 (6H, d, J=7 Hz, $OCH_2CH(C\underline{H}_3)_2$), 2.09 (1H, m, $OCH_2C\underline{H}(CH_3)_2$), 3.86 (2H, d, J=7 Hz, $OC\underline{H}_2CH(CH_3)_2$), 6.88-7.32 (3H, m, Ar—H), 8.01 (1H, d, J=8 Hz, Ar—H), 8.59 (1H, s, $C_4$—H), 6.60-12.00 (3H, b, 2×NH, OH).

Mass m/e: 303 (M+).

EXAMPLE 53

Ethyl 1,6-dihydro-2-(3-methoxyanilino)-6-oxo-5-pyrimidinecarboxylate (3 g) and sodium hydroxide (1 g) are added to water (50 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (60 ml), and the mixture is refluxed with stirring for 1 hour. After cooling, the resulting product is collected by filtration and dried at 80° C. under reduced pressure to give 1,6-dihydro-2-(3-methoxyanilino)-6-oxo-5-pyrimidinecarboxylic acid (1.8 g). M.p. 247°-249° C.

Elemental analysis for $C_{12}H_{11}N_3O_4$: Calcd. (%): C, 55.17; H, 4.24; N, 16.09. Found (%): C, 54.84; H, 4.09; N, 15.79.

IR $\nu_{max}^{nujol}$ $cm^{-1}$: 2400-3200 (NH, OH), 1670 (C=O), 1630 (C=O).

NMR (DMSO-$d_6$) δ: 3.84 (3H, s, $OCH_3$), 6.80 (1H, dd, $J_1$=8 Hz, $J_2$=4 Hz, Ar—H), 7.06-7.48 (3H, m, Ar—H), 8.56 (1H, s, $C_4$—H), 3.60-10.20 (3H, b, 2×NH, OH).

Mass m/e: 261 (M+).

EXAMPLE 54

Ethyl 1,6-dihydro-2-(4-ethoxyanilino)-6-oxo-5-pyrimidinecarboxylate (10 g) and sodium hydroxide (3 g) are added to water (50 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (50 ml), and the mixture is refluxed with stirring for 1 hour. After cooling, the resulting product is collected by filtration and dried at 80° C. under reduced pressure to give 1,6-dihydro-2-(4-ethoxyanilino)-6-oxo-5-pyrimidinecarboxylic acid (5 g). M.p. 250°-252° C.

Elemental analysis for $C_{13}H_{13}N_3O_4$: Calcd. (%): C, 56.72; H, 4.76; N, 15.27. Found (%): C, 56.82; H, 4.63; N, 15.17.

IR $\nu_{max}^{nujol}$ $cm^{-1}$: 2400-3200 (NH, OH), 1700 (C=O), 1660 (C=O).

NMR (DMSO-$d_6$) δ: 1.32 (3H, t, J=7 Hz, $OCH_2C\underline{H}_3$), 4.04 (2H, q, J=7 Hz, $OC\underline{H}_2CH_3$), 6.94 (2H, d, J=8 Hz, Ar—H), 7.42 (2H, d, J=8 Hz, Ar—H), 8.40 (1H, s, $C_4$—H), 3.60-11.40 (3H, b, 2×NH, OH).

Mass m/e: 275 (M+).

EXAMPLE 55

Ethyl 1,6-dihydro-2-(2,5-dimethoxyanilino)-6-oxo-5-pyrimidinecarboxylate (6 g) and sodium hydroxide (2 g) are added to water (100 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (50 ml), and the mixture is refluxed with stirring for 1 hour. After cooling, the resulting product is collected by filtration and dried at 80° C. under reduced pressure to give 1,6-dihydro-2-(2,5-dimethoxyanilino)-6-oxo-5-pyrimidinecarboxylic acid (3.7 g). M.p. 260°-262° C.

Elemental analysis for $C_{13}H_{13}N_3O_5$: Calcd. (%): C, 53.61; H, 4.50; N, 14.43. Found (%): C, 53.61; H, 4.41; N, 14.21.

$IR_{max}^{nujol}$ $cm^{-1}$: 2400-3300 (NH, OH), 1715 (C=O), 1630 (C=O).

NMR (DMSO-$d_6$): 3.76 (3H, 3, $OCH_3$), 3.88 (3H, 3, $OCH_3$), 6.72 (1H, dd, $J_1$=8 Hz, $J_2$=4 Hz, Ar—H), 7.04 (1H, d, J=8 Hz, Ar—H), 7.94 (1H, d, J=4 Hz, Ar—H), 8.60 (1H, s, $C_4$—H), 5.00-11.00 (3H, b, 2×NH, OH).

Mass m/e: 291 (M+).

EXAMPLE 56

Ethyl 1,6-dihydro-2-(3,4-diethoxyanilino)-6-oxo-5-pyrimidinecarboxylate (5 g) and sodium hydroxide (2 g) are added to water (50 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (40 ml), and the mixture is refluxed with stirring for 1 hour. After cooling, the resulting product is collected by filtration and dried at 80° C. under reduced pressure to give 1,6-dihydro-2-(3,4-diethoxyanilino)-6-oxo-5-pyrimidinecarboxylic acid (3 g). M.p. 243°-245° C.

Elemental analysis for $C_{15}H_{17}N_3O_5$: Calcd. (%): C, 56.42; H, 5.37; N, 13.16. Found (%): C, 56.66; H, 5.36; N, 13.15.

IR $\nu_{max}^{nujol}$ $cm^{-1}$: 2400–3400 (NH, OH), 1720 (C=O), 1660 (C=O).

NMR (DMSO-$d_6$) δ: 1.36 (6H, t=7 Hz, $OCH_2\underline{CH_3}$), 4.08 (4H, q, J=7 Hz, $O\underline{CH_2}CH_3$), 6.96–7.20 (3H, m, Ar—H), 8.56 (1H, s, $C_4$—H), 5.00–11.80 (3H, b, 2×NH, OH).

Mass m/e: 319 (M+).

EXAMPLE 57

Ethyl 1,6-dihydro-2-(2,5-dimethylanilino)-6-oxo-5-pyrimidinecarboxylate (10 g) and sodium hydroxide (4 g) are added to water (200 ml), and the mixture is refluxed with stirring for 2 hours. After cooling, the reaction mixture is acidified with acetic acid, and the resulting solid is collected by filtration and recrystallized from DMF. The precipitate is collected by filtration and added to water (100 ml), and the mixture is refluxed with stirring for 1 hour. After cooling, the resulting product is collected by filtration and dried at 80° C. under reduced pressure to give 1,6-dihydro-2-(2,5-dimethylanilino)-6-oxo-5-pyrimidinecarboxylic acid (7 g). M.p. 242°–244° C.

Elemental analysis for $C_{13}H_{13}N_3O_3$: Calcd. (%): C, 59.76; H, 5.79; N, 16.08. Found (%): C, 59.88; H, 5.68; N, 16.30.

IR $\nu_{max}^{nujol}$ $cm^{-1}$: 2400–3300 (NH, OH), 1715 (C=O), 1630 (C=O).

NMR (DMSO-$d_6$) δ: 2.22 (3H, s, $CH_3$), 2.31 (3H, s, $CH_3$), 7.05 (1H, d, J=8 Hz, Ar—H), 7.22 (1H, d, J=8 Hz, Ar—H), 8.52 (1H, s, $C_4$—H), 9.40–11.20 (3H, b, 2×NH, OH).

Mass m/e: 259 (M+).

EXAMPLE 58

Ethyl 1,6-dihydro-6-oxo-2-(3-trifluoromethylanilino)-5-pyrimidinecarboxylate (34.4 g) and sodium hydroxide (10 g) are added to water (300 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (300 ml), and the mixture is refluxed with stirring for 1 hour. After cooling, the resulting product is collected by filtration and dried at 80° C. under reduced pressure to give 1,6-dihydro-6-oxo-2-(3-trifluoromethylanilino)-5-pyrimidinecarboxylic acid (21.5 g). M.p. 252°–254° C.

Elemental analysis for $C_{12}H_8N_3O_3F_3$: Calcd. (%): C, 48.16; H, 2.68; N, 14.05. Found (%): C, 48.15; H, 2.86; N, 14.28.

IR $\nu_{max}^{nujol}$ $cm^{-1}$: 2200–3400 (NH, OH), 1725 (C=O), 1650 (C=O).

NMR (DMSO-$d_6$) δ: 7.40–8.00 (3H, m, Ar—H), 8.12 (1H, s, Ar—H), 8.58 (1H, s, $C_4$—H), 6.00–12.00 (3H, b, 2×NH, OH).

Mass m/e: 299 (M+).

EXAMPLE 59

Ethyl 1,6-dihydro-2-[4-(N,N-dimethylamino)anilino]-6-oxo-5-pyrimidinecarboxylate (7.5 g) and sodium hydroxide (3.0 g) are added to water (150 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (50 ml), and the mixture is refluxed with stirring for 1 hour. After cooling, the resulting product is collected by filtration and dried at 80° C. under reduced pressure to give 1,6-dihydro-2-[4-(N,N-dimethylamino)anilino]-6-oxo-5-pyrimidinecarboxylic acid (5 g). M.p. 261°–263° C.

Elemental analysis for $C_{13}H_{14}N_4O_3$: Calcd. (%): C, 56.93; H, 5.13; N, 20.43. Found (%): C, 57.20; H, 5.17; N, 20.68.

IR $\nu_{max}^{nujol}$ $cm^{-1}$: 2400–3300 (NH, OH), 1710 (C=O), 1620 (C=O).

NMR (DMSO-$d_6$) δ: 2.96 (6H, s, $N(CH_3)_2$), 6.84 (2H, d, J=8 Hz, Ar—H), 7.40 (2H, d, J=8 Hz, Ar—H), 8.52 (1H, s, $C_4$—H), 4.40–12.00 (3H, b, 2×NH, OH).

Mass m/e: 274 (M+).

EXAMPLE 60

Ethyl 1,6-dihydro-2-(2-hydroxyanilino)-6-oxo-5-pyrimidinecarboxylate (5 g) and sodium hydroxide (2 g) are added to water (100 ml), and the mixture is refluxed with stirring for 1 hour. After cooling, the reaction mixture is acidified with acetic acid, and the resulting solid is collected by filtration and recrystallized from DMF. The precipitate is collected by filtration and added to water (100 ml), and the mixture is refluxed with stirring for 1 hour. After cooling, the resulting product is collected by filtration and dried at 80° C. under reduced pressure to give 1,6-dihydro-2-(2-hydroxyanilino)-6-oxo-5-pyrimidinecarboxylic acid (3 g). M.p. 254°–256° C.

Elemental analysis for $C_{11}H_9N_3O_4$: Calcd. (%): C, 53.44; H, 3.69; N, 17.00. Found (%): C, 53.52; H, 3.55; N, 17.00.

IR $\nu_{max}^{nujol}$ $cm^{-1}$: 2200–3400 (NH, OH), 1720 (C=O), 1650 (C=O).

NMR (DMSO-$d_6$) δ: 6.70–7.16 (3H, m, Ar—H), 8.02 (1H, d, J=7 Hz, Ar—H), 8.53 (1H, s, $C_4$—H), 8.60–10.00 (3H, b, 2×NH, OH).

Mass m/e: 247 (M+).

EXAMPLE 61

Ethyl 1,6-dihydro-2-(2-fluoroanilino)-6-oxo-5-pyrimidinecarboxylate (5 g) and sodium hydroxide (2 g) are added to water (100 ml), and the mixture is refluxed with stirring for 1 hour. After cooling, the reaction mixture is acidified with acetic aicd, and the resulting solid is collected by filtration and recrystallized from DMF. The precipitate is collected by filtration and added to water (70 ml), and the mixture is refluxed with stirring for 1 hour. After cooling, the resulting product is collected by filtration and dried at 80° C. under reduced pressure to give 1,6-dihydro-2-(2-fluoroanilino)-6-oxo-5-pyrimidinecarboxylic acid (3.1 g). M.p. 300° C.

Elemental analysis for $C_{11}H_{18}N_3O_3F$: Calcd. (%): C, 53.10; H, 3.21; N, 16.87. Found (%): C, 52.87; H, 3.31; N, 16.68.

IR $\nu_{max}^{nujol}$ $cm^{-1}$: 2400–3300 (NH, OH), 1680 (C=O), 1620 (C=O).

NMR (DMSO-$d_6$) δ: 7.04–7.44 (3H, m, Ar—H), 7.96–8.20 (1H, m, Ar—H), 8.61 (1H, s, $C_4$—H), 9.00–10.08 (3H, b, 2×NH, OH).

Mass m/e: 249 (M+).

In the same manner as described in Example 61, ethyl 1,6-dihydro-2-anilino-6-oxo-5-pyrimidinecarboxylate derivatives are hydrolyzed with an alkali to give the corresponding compounds of Examples 62 to 88. The compounds thus obtained and analytical data thereof are shown in Table 3.

TABLE 3

Compounds

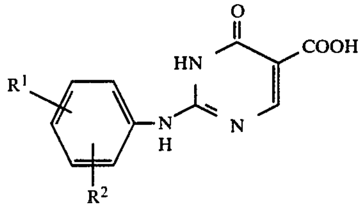

| Ex. No. | $R^1$ (binding position) | $R^2$ (binding position) | M.p. (°C.) | IR $\nu_{max}^{nujol}$ $cm^{-1}$ (c = 0) | Mass m/e ($M^+$) | NMR ($DMSO-d_6$) $\delta(C_4—H)$ |
|---|---|---|---|---|---|---|
| 62 | H | $O(CH_2)_4CH_3$ (2-position) | 198–200 | 1630, 1720 | 317 | 8.54 |
| 63 | H | $O(CH_2)_2CH(CH_3)_2$ (2-position) | 215–216 | 1650, 1710 | 317 | 8.59 |
| 64 | H | $O(CH_2)_5CH_3$ (2-position) | 186–188 | 1640, 1720 | 331 | 8.59 |
| 65 | H | $O(CH_2)_6CH_3$ (2-position) | 167–169 | 1600, 1715 | 345 | 8.54 |
| 66 | H | $O(CH_2)_2CH_3$ (3-position) | 186–188 | 1660, 1720 | 286 | 8.50 |
| 67 | H | $O(CH_2)_3CH_3$ (3-position) | 183–185 | 1660, 1705 | 303 | 8.50 |
| 68 | H | $O(CH_2)_4CH_3$ (3-position) | 169–170 | 1660, 1705 | 317 | 8.52 |
| 69 | H | $O(CH_2)_2CH_3$ (4-position) | 249–250 | 1630, 1700 | 289 | 8.52 |
| 70 | H | $OCH(CH_3)_2$ (4-position) | 248–250 | 1660, 1700 | 289 | 8.48 |
| 71 | H | $O(CH_2)_3CH_3$ (4-position) | 246–248 | 1660, 1705 | 303 | 8.48 |
| 72 | H | $OCH_2CH(CH_3)_2$ (4-position) | 248–250 | 1660, 1700 | 303 | 8.47 |
| 73 | H | $O(CH_2)_4CH_3$ (4-position) | 243–245 | 1670, 1705 | 317 | 8.47 |
| 74 | H | $O(CH_2)_2CH(CH_3)_2$ (4-position) | 240–242 | 1660, 1705 | 317 | 8.48 |
| 75 | H | $O(CH_2)_5CH_3$ (4-position) | 228–230 | 1670, 1705 | 331 | 8.48 |
| 76 | $OCH_2CH_3$ (2-position) | $OCH_2CH_3$ (5-position) | 251–253 | 1620, 1700 | 319 | 8.63 |
| 77 | $O(CH_2)_2CH_3$ (2-position) | $O(CH_2)_2CH_3$ (5-position) | 228–230 | 1630, 1715 | 347 | 8.64 |
| 78 | $OCH(CH_3)_2$ (2-position) | $OCH(CH_3)_2$ (5-position) | 206–208 | 1640, 1720 | 347 | 8.64 |
| 79 | $O(CH_2)_3CH_3$ (2-position) | $O(CH_2)_3CH_3$ (5-position) | 180–182 | 1620, 1710 | 375 | 8.58 |
| 80 | $OCH_2CH(CH_3)_2$ (2-position) | $OCH_2CH(CH_3)_2$ (5-position) | 206–208 | 1620, 1700 | 375 | 8.64 |
| 81 | $O(CH_2)_2CH_3$ (3-position) | $O(CH_2)_2CH_3$ (4-position) | 229–231 | 1670, 1720 | 347 | 8.59 |
| 82 | $O(CH_2)_3CH_3$ (3-position) | $O(CH_2)_3CH_3$ (4-position) | 226–228 | 1650, 1700 | 375 | 8.54 |
| 83 | H | $(CH_2)_3CH_3$ (4-position) | 212–214 | 1640, 1680 | 287 | 8.52 |
| 84 | H | $CH_2CH_3$ (4-position) | 248–250 | 1630, 1720 | 259 | 8.48 |
| 85 | $CH_3$ (2-position) | $CH_3$ (3-position) | 249–251 | 1630, 1720 | 259 | 8.48 |
| 86 | H | F (3-position) | 270–272 | 1640, 1680 | 249 | 8.54 |
| 87 | H | Br (4-position) | 247–248 | 1640, 1680 | 309 | 8.62 |
| 88 | H | 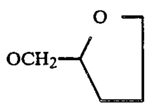 (2-position) | 220–222 | 1640, 1725 | 331 | 8.48 |

EXAMPLE 89

A mixture of ethyl 1,6-dihydro-2-methylthio-6-oxo-5-pyrimidinecarboxylate (5 g) and aniline (2.6 g) is heated without solvent at 130° C. for 1 hour. After cooling, the resulting solid is pulverized and recrystallized from DMSO to give ethyl 2-anilino-1,6-dihydro-6-oxo-5-pyrimidinecarboxylate (3.7 g). M.p. 267°–269° C.

Elemental analysis for $C_{13}H_{13}N_3O_3$: Calcd. (%): C, 60.23; H, 5.05; N, 16.21. Found (%): C, 59.99; H, 5.09; N, 15.89.

IR $\nu_{max}^{nujol}$ $cm^{-1}$: 2400–3350 (NH), 1710 (C=O), 1660 (C=O).

NMR (DMSO-$d_6$) δ: 1.28 (3H, t, J=8 Hz, $OCH_2C\underline{H}_3$), 4.26 (2H, q, J=8 Hz, $OC\underline{H}_2CH_3$), 7.00–7.74 (5H, m, Ar—H), 8.10 (2H, b, 2×NH) 8.48 (1H, s, $C_4$—H).

EXAMPLE 90

Sodium hydrogen carbonate (0.82 g) is dissolved in water (50 ml), and thereto is added 1,6-dihydro-6-oxo-2-(3-trifluoromethylanilino)-5-pyrimidinecarboxylic acid (3 g), and the mixture is heated. After foaming is finished, ethanol is added to the reaction mixture, and the solution is allowed to stand overnight. The precipitate is collected by filtration and recrystallized from a mixture of methanol and water to give sodium 1,6-dihydro-6-oxo-2-(3-trifluoromethylanilino)-5-pyrimidinecarboxylate (2.4 g). M.p. 256°–259° C.

Elemental analysis for $C_{12}H_7N_3O_3F_3Na.H_2O$: Calcd. (%): C, 42.48; H, 2.65; N, 12.39. Found (%): C, 42.43; H, 2.68; N, 12.22.

IR $\nu_{max}^{nujol}$ $cm^{-1}$: 2800–3400 (NH), 1680 (C=O), 1610 (C=O).

NMR (DMSO-$d_6$) δ: 3.50 (1H, b, NH), 7.21 (1H, d, J=8 Hz, Ar—H), 7.50 (1H, t, J=8 Hz, Ar—H), 8.05 (1H, d, J=8 Hz, Ar—H), 8.34 (1H, s, Ar—H), 8.52 (1H, s, $C_4$—H), 9.51 (1H, bs, NH).

EXAMPLE 91

A mixture of 1,6-dihydro-2-[2-(2-methylpropoxy)anilino]-6-oxo-5-pyrimidinecarboxylic acid (20 g) and sodium carbonate (7.0 g) in ethanol (100 ml) and water (100 ml) is heated until the solution is completed. After allowing to stand the solution overnight, the precipitate is collected by filtration, washed with water and dried to give sodium 1,6-dihydro-2-[2-(2-methylpropoxy)anilino]-6-oxo-5-pyrimidinecarboxylate (12.4 g). M.p. 231°–233° C.

Elemental analysis for $C_{15}H_{16}N_3O_4Na$: Calcd. (%): C, 55.38; H, 4.96; N, 12.92. Found (%): C, 55.14; H, 4.93; N, 12.77.

IR $\nu_{max}^{nujol}$ $cm^{-1}$: 2400–3400 (NH), 1665 (C=O), 1625 (C=O).

NMR (DMSO-$d_6$) δ: 1.04 (6H, d, J=7 Hz, $OCH_2CH(CH_3)_2$), 2.16 (1H, m, $OCH_2C\underline{H}(CH_3)_2$), 3.84 (2H, d, J=7 Hz, $OC\underline{H}_2CH(CH_3)_2$), 6.94 (3H, m, Ar—H), 7.59 (1H, b, NH), 8.44 (1H, s, $C_4$—H), 8.50 (1H, m, Ar—H), 12.20–12.80 (1H, b, NH). Mass m/e: 327 (M+).

EXAMPLE 92

To a solution of N-(2-propoxyphenyl)guanidine (9.1 g) in dioxane (30 ml) is added dropwise diethyl ethoxymethylenemalonate (10.2 g), and the mixture is refluxed with stirring for 5 hours. After cooling, the precipitate is collected by filtration and recrystallized from a mixture of DMF and water to give ethyl 1,6-dihydro-6-oxo-2-(2-propoxyanilino)-5-pyrimidinecarboxylate (11.7 g). M.p. 198°–200° C.

Elemental analysis for $C_{16}H_{19}N_3O_4$: Calcd. (%): C, 60.56; H, 6.03; N, 13.29. Found (%): C, 60.81; H, 5.97; N, 13.48.

IR $\nu_{max}^{nujol}$ $cm^{-1}$: 3000–3300 (NH), 1720 (C=O), 1600 (C=O).

NMR (DMSO-$d_6$) δ: 1.00 (3H, t, J=7 Hz, $OCH_2CH_2C\underline{H}_3$), 1.28 (3H, t, J=7 Hz, $OCH_2C\underline{H}_3$), 1.80 (2H, m, $OCH_2C\underline{H}_2CH_3$), 4.10 (2H, t, J=7 Hz, $OC\underline{H}_2CH_2CH_3$), 4.25 (2H, q, J=7 Hz, $OC\underline{H}_2CH_3$), 6.80–7.30 (3H, m, Ar—H), 8.23 (1H, d, J=8 Hz, Ar—H), 8.52 (1H, s, $C_4$—H), 7.90–14.00 (2H, b, 2×NH).

Mass m/e: 317 (M+).

EXAMPLE 93

A mixture of N-(2-butoxyphenyl)guanidine (11.6 g) and diethyl ethoxymethylenemalonate (12.1 g) in DMF (70 ml) is heated at 100° C. for 9 hours. After cooling, water (50 ml) is added to the reaction mixture, and the precipitate is collected by filtration, washed with ethanol and recrystallized from a mixture of DMF and water to give ethyl 2-(2-butoxyanilino)-1,6-dihydro-6-oxo-5-pyrimidinecarboxylate (16.1 g). M.p. 211°–213° C.

Elemental analysis for $C_{17}H_{21}N_3O_4$: Calcd. (%): C, 61.62; H, 6.39; N, 12.68. Found (%): C, 61.39; H, 6.45; N, 12.73.

IR $\nu_{max}^{nujol}$ $cm^{-1}$: 2600–3200 (NH), 1720 (C=O), 1600 (C=O).

NMR (DMSO-$d_6$) δ: 0.94 (3H, t, J=7 Hz, $OCH_2CH_2CH_2C\underline{H}_3$), 1.27 (3H, t, J=7 Hz, $OCH_2C\underline{H}_3$), 1.46 (2H, m, $OCH_2CH_2C\underline{H}_2CH_3$), 1.72 (2H, m, $OCH_2C\underline{H}_2CH_2CH_3$), 4.12 (2H, t, J=7 Hz, $OC\underline{H}_2CH_2CH_2CH_3$), 4.30 (2H, q, J=7 Hz, $OC\underline{H}_2CH_3$), 6.90–7.40 (3H, m, Ar—H), 8.16 (1H, d, J=8 Hz, Ar—H), 8.50 (1H, s, $C_4$—H), 6.80–11.70 (2H, b, 2×NH).

Mass m/e: 331 (M+).

EXAMPLE 94

Diethyl morpholinomethylenemalonate (20.0 g) is added to a solution of N-[2-(2-methylpropoxy)phenyl]-guanidine (16.1 g) and potassium carbonate (21.5 g) in ethanol (40 ml) and water (40 ml), and the mixture is heated with stirring at 60° C. for 3 hours. After the reaction is completed, water (100 ml) is added to the reaction mixture with stirring under water-cooling, and the mixture is acidified to pH 3 with 10% aqueous HCl. The resulting precipitate is collected by filtration and dissolved in chloroform (300 ml). The chloroform layer is washed with water twice, dried over anhydrous sodium sulfate and then concentrated under reduced pressure. The residue is recrystallized from DMF to give ethyl 1,6-dihydro-2-[2-(2-methylpropoxy)anilino]-6-oxo-5-pyrimidinecarboxylate (16.0 g). M.p. 175°–177° C.

Elemental analysis for $C_{17}H_{21}N_3O_4$: Calcd. (%): C, 61.62; H, 6.39; N, 12.68. Found (%): C, 61.96; H, 6.35; N, 12.44.

IR $\nu_{max}^{nujol}$ $cm^{-1}$: 2600–3300 (NH), 1730 (C=O), 1620 (C=O).

NMR (DMSO-$d_6$) δ: 1.03 (6H, d, J=7 Hz, $OCH_2CH(C\underline{H}_3)_2$), 1.28 (3H, t, J=7 Hz, $OCH_2C\underline{H}_3$), 2.10 (1H, m, $OCH_2C\underline{H}(CH_3)_2$), 3.81 (2H, d, J=7 Hz, $OC\underline{H}_2CH(CH_3)_2$), 4.18 (2H, q, J=7 Hz, $OC\underline{H}_2CH_3$), 6.80–7.22 (3H, m, Ar—H), 8.10 (1H, d, J=8 Hz, Ar—H), 8.40 (1H, s, $C_4$—H), 8.50–12.50 (2H, b, 2×NH).

Mass m/e: 331 (M+).

This product has polymorphic forms as is shown in the following example, and hence, even though they are the same substance, they are somewhat different in some physical properties such as the melting point, IR spectrum or the like.

EXAMPLE 95

To a solution of N-[2-(2-methylpropoxy)phenyl]-guanidine (89 g) in denatured alcohol (300 ml) is added dropwise diethyl ethoxymethylenemalonate (93 g), and the mixture is refluxed with stirring for 3 hours. After cooling, the precipitate is collected by filtration, washed with denatured alcohol and petroleum ether and dried to give ethyl 1,6-dihydro-2-[2-(2-methylpropoxy)anilino]-6-oxo-5-pyrimidinecarboxylate (94 g). M.p. 188°-190° C.

Elemental analysis for $C_{17}H_{21}N_3O_4$: Calcd. (%): C, 61.62; H, 6.39; N, 12.68. Found (%): C, 61.45; H, 6.33; N, 12.70.

IR $\nu_{max}^{nujol}$ $cm^{-1}$: 2600-3240 (NH), 1705 (C=O), 1650 (C=O).

NMR (DMSO-$d_6$) δ: 1.05 (6H, d, J=7 Hz, $OCH_2CH(CH_3)_2$), 2.10 (1H, m, $OCH_2CH(CH_3)_2$), 3.81 (2H, d, J=7 Hz, $OCH_2CH(CH_3)_2$), 4.18 (2H, q, J=7 Hz, $OCH_2CH_3$), 6.81-7.25 (3H, m, Ar—H), 8.10 (1H, d, J=8 Hz, Ar—H), 8.42 (1H, s, $C_4$—H), 8.50-12.50 (2H, b, 2×NH).

Mass m/e: 331 (M+).

EXAMPLE 96

A mixture of N-(3-trifluoromethylphenyl)guanidine (10 g), diethyl N,N-diethylaminomalonate (11.8 g) and potassium carbonate (13.4 g) in water (100 ml) and ethanol (100 ml) is refluxed with stirring for 7 hours. After cooling, the mixture is acidified to pH 3 with 10% aqueous HCl. The precipitate is collected by filtration, washed with water and recrystallized from a mixture of DMF and water to give ethyl 1,6-dihydro-6-oxo-2-(3-trifluoromethylanilino)-5-pyrimidinecarboxylate (13.4 g). M.p. 229°-231° C.

Elemental analysis for $C_{14}H_{12}N_3O_3F_3$: Calcd. (%): C, 51.38; H, 3.67; N, 12.84. Found (%): C, 51.22; H, 3.83; N, 12.97.

IR $\nu_{max}^{nujol}$ $cm^{-1}$: 2500-3400 (NH), 1720 (C=O), 1605 (C=O).

NMR (DMSO-$d_6$) δ: 1.30 (3H, t, J=7 Hz, $OCH_2CH_3$), 4.26 (2H, q, J=7 Hz, $OCH_2CH_3$), 7.40-8.20 (4H, m, Ar—H), 8.60 (1H, s, $C_4$—H), 9.00-12.50 (2H, b, 2×NH).

Mass m/e: 327 (M+).

EXAMPLES 97 TO 103

In the same manner as described in Example 92, the corresponding N-substituted phenylguanidine and diethyl ethoxymethylenemalonate are reacted to give the compounds as shown in Table 4.

TABLE 4

Compounds

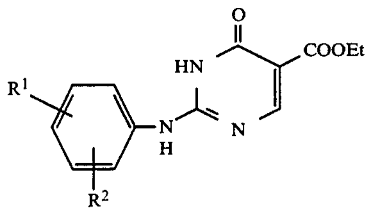

| Ex. No. | $R^1$ | $R^2$ | M.p. (°C.) | IR $\nu_{max}^{nujol}$ $cm^{-1}$ (c = 0) | Mass m/e ($M^+$) | NMR (DMSO-$d_6$) δ($C_4$—H) |
|---|---|---|---|---|---|---|
| 97 | H | 2-$CH_3O$ | 217-219 | 1660, 1720 | 289 | 8.42 |
| 98 | H | 2-$(CH_3)_2CHO$ | 206-208 | 1600, 1720 | 317 | 8.54 |
| 99 | H | 4-$CH_3CH_2$ | 265-267 | 1650, 1680 | 287 | 8.43 |
| 100 | H | 3-Cl | 270-272 | 1650, 1720 | 293 | 8.59 |
| 101 | H | 4-$(CH_3)_2N$— | 246-248 | 1640, 1730 | 302 | 8.45 |
| 102 | 2-$CH_3$ | 5-$CH_3$ | 252-254 | 1640, 1690 | 287 | 8.40 |
| 103 | 2-$CH_3O$ | 5-$CH_3O$ | 221-223 | 1605, 1720 | 319 | 8.48 |

| Preparation 1 | |
|---|---|
| 1,6-Dihydro-2-[2-(2-methylpropoxy)anilino]-6-oxo-5-pyrmidinecarboxylic acid | 50 mg |
| Lactose | 190 mg |
| Crystalline cellulose | 50 mg |
| Magnesium stearate | 10 mg |

A mixture of the above components is tabletted in a usual manner to give tablets containing the active ingredient of 50 mg per each tablet.

| Preparation 2 | |
|---|---|
| 1,6-Dihydro-2-(2-propoxyanilino)-6-oxo-5-pyrmidinecarboxylic acid | 25 mg |
| Magnesium stearate | 5 mg |
| Lactose | 135 mg |
| Potato starch | 50 mg |
| Talc | 35 mg |

A mixture of the above components is granulated in a usual manner to give granules containing 10% of the active ingredient.

Preparation 3

The granules obtained in Preparation 2 are packed into 1# hard capsules to give capsules containing the active ingredient of 25 mg per each capsule.

| Preparation 4 | |
|---|---|
| Sodium 1,6-dihydro-6-oxo-2-(3-trifluoromethyl-anilino)-5-pyrmidinecarboxylate | 25 mg |
| Solubilizer (if necessary) | q.s. |
| Sodium chloride (if necessary) | q.s. |
| Distilled water for injection | 1 ml |
| Totally | 1 ml |

The active ingredient, solubilizer and sodium chloride are dissolved in the distilled water, and the solution is entered into an ampoule, which is sterilized to give an injection ampoule.

| Preparation 5 | |
|---|---|
| Sodium 1,6-dihydro-2-[2-(2-methylpropoxy)-anilino]-6-oxo-5-pyrmidinecarboxylate | 50 mg |
| Lactose | 190 mg |
| Crystalline cellulose | 50 mg |
| Magnesium stearate | 10 mg |

A mixture of the above components is tabletted in a usual manner to give tablets containing the active ingredient of 50 mg per each tablet.

| Preparation 6 | |
|---|---|
| Sodium 1,6-dihydro-2-[2-(2-methylpropoxy)-anilino]-6-oxo-5-pyrmidinecarboxylate | 5 mg |
| Solubilizer (if necessary) | q.s. |
| Sodium chloride (if necessary) | q.s. |
| Distilled water for injection | 1 ml |
| Totally | 1 ml |

The active ingredient, solubilizer and sodium chloride are dissolved in the distilled water, and the solution is entered into an ampoule, which is sterilized to give an injection ampoule.

Pharmacological Test

[1] PCA response in rats:

Wistar male rats weighing 190–220 g were used. A diluted anti-dinitrophenyl-Ascalis (DNP-As) rat serum (each 0.1 ml) was intracutaneously injected into the back of the animals, by which the animals were passively sensitized. After 48 hours, Evans blue liquid (1.0 ml) containing DNP-As (20 mg, as a protein) was intravenously injected to the animals to induce PCA.

After 30 minutes, rats were killed, and the skin at the response region was peeled off, and the amount of color was measured spectrophotometrically. Test compounds were administered 30 minutes (in case of intraperitoneal injection) or one hour (in case of oral administration) before the challenge with the antigen.

The 50% inhibiting dose ($ED_{50}$) of representative compounds in the rat PCA is shown in Table 5. The data of the references: disodium chromoglycate (SDCG) and Tranilast are also shown therein.

TABLE 5

Compound

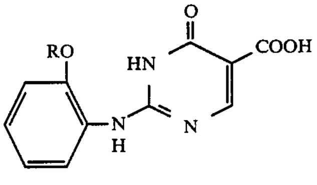

| Ex. No. of compound | R | $ED_{50}$ (mg/kg) i.p. | p.o. |
|---|---|---|---|
| 48 | $CH_2CH_3$ | 20.2 | 98.0 |
| 49 | $CH_2CH_2CH_3$ | 11.0 | 22.2 |
| 50 | $CH(CH_3)_2$ | 13.0 | 75 |
| 51 | $CH_2CH_2CH_2CH_3$ | 10.7 | 92 |
| 52 | $CH_2CH(CH_3)_2$ | 4.7 | 39 |
| | DSCG | 3.3 | >200 |

TABLE 5-continued

Compound

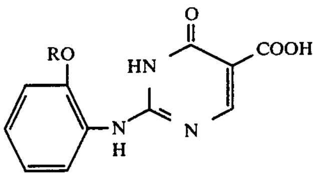

| Ex. No. of compound | R | $ED_{50}$ (mg/kg) i.p. | p.o. |
|---|---|---|---|
| | Tranilast | 40 | 110 |

[2] Anti-SRS-A action:

The anti-SRS-A activity of the compounds of the present invention was measured by Magnus method using the isolated guinea pig ileum. An extracted ileum of guinea pig was hung within a Magnus vessel which was maintained at 31±1° C. and then pre-treated with mepiramine to remove any effect by histamine. Test compound was administered in a dose of $3\times10^{-5}$ to $10^{-3}$M, and after 3 minutes, a previously prepared crude SRS-A was acted thereto, and then, the shrink rate (%) of the ileum was measured. The results as to the representative compounds are shown in Table 6. The data as to the references: DSCG and Tranilast are also shown in the table.

TABLE 6

Compound

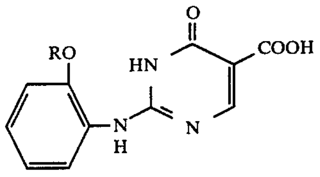

| Ex. No. of compound | R | Concentration of test compd. (M) | Inhibition rate (%) | 50% inhibition concentration (M) |
|---|---|---|---|---|
| 49 | $CH_2CH_2CH_3$ | $10^{-4}$ | 8.1 | $4.87\times10^{-4}$ |
| | | $3\times10^{-4}$ | 17.9 | |
| | | $10^{-3}$ | 97.3 | |
| 52 | $CH_2CH(CH_3)_2$ | $3\times10^{-5}$ | 12.2 | $1.54\times10^{-4}$ |
| | | $10^{-4}$ | 26.2 | |
| | | $3\times10^{-4}$ | 87.9 | |
| | Tranilast | $10^{-4}$ | 23.5 | $>10^{-3}$ |
| | | $3\times10^{-4}$ | 32.4 | |
| | | $10^{-3}$ | 48.2 | |
| | DSCG | $10^{-3}$ | 6 | $>10^{-3}$ |

Toxicity Test

The test compound was suspended in 0.5% carboxymethylcellulose solution, and the suspension was intraperitoneally administered to ddY male mice (weighing 20–25 g, one group: 10 mice). Based on the total mortality during 7 days after the administration of the test compound, the 50% lethal dose ($LD_{50}$) was calculated by Litchfield-Wilcoxon method. The results of the representative compounds are shown in Table 7. The data of reference (Tranilast) are also shown therein.

TABLE 7

Compound

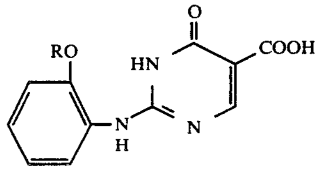

| Ex. No. of compound | R | $LD_{50}$ (mg/kg) i.p. | p.o. |
|---|---|---|---|
| 48 | $CH_2CH_3$ | >500 | >3000 |
| 49 | $CH_2CH_2CH_3$ | 1160 | >3000 |
| 51 | $CH_2CH_2CH_2CH_3$ | 1230 | >3000 |
| 52 | $CH_2CH(CH_3)_2$ | 780 | >3000 |
| | Tranilast | 430 | 780 |

What is claimed is:

1. A 2-anilino-1,6-dihydro-6-oxo-5-pyrimidine-carboxylic acid compound of the formula:

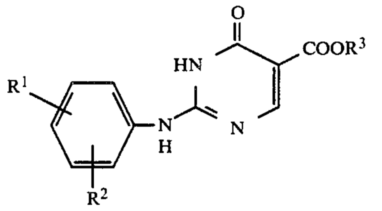

(I)

wherein $R^1$ is hydrogen, $R^2$ is an alkoxy having 1 to 7 carbon atoms, and $R^3$ is hydrogen or an alkyl having 1 to 4 carbon atoms, or a pharmaceutically acceptable salt thereof.

2. The compound according to claim 1, wherein $R^1$ is hydrogen, $R^2$ is an alkoxy having 1 to 7 carbon atoms and $R^3$ is an alkyl having 1 to 4 carbon atoms.

3. The compound according to claim 1, wherein $R^1$ and $R^3$ are hydrogen and $R^2$ is an alkoxy having 1 to 7 carbon atoms.

4. The compound according to claim 1, wherein $R^1$ and $R^3$ are hydrogen and $R^2$ is 2-alkoxy having 1 to 7 carbon atoms.

5. The compound according to claim 1, wherein $R^1$ is hydrogen, $R^2$ is 2-alkoxy having 1 to 7 carbon atoms and $R^3$ is an alkali metal.

6. The compound according to claim 1, which is 1,6-dihydro-2-[2-(2-methylpropoxy)anilino]-6-oxo-5-pyrimidinecarboxylic acid.

7. The compound according to claim 1, which is sodium 1,6-dihydro-2-[2-(2-methylpropoxy)anilino]-6-oxo-5-pyrimidinecarboxylate.

8. An antiallergic composition which comprises as an active ingredient an effective amount of a 2-anilino-1,6-dihydro-6-oxo-5-pyrimidinecarboyxlic acid compound of the formula:

(I)

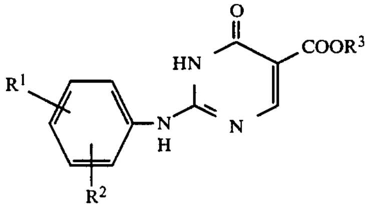

wherein $R^1$ is hydrogen $R^2$ is an alkoxy having 1 to 7 carbon atoms, and $R^3$ is hydrogen or an alkyl having 1 to 4 carbon atoms, or a pharmaceutically acceptable salt thereof in admixture with a conventional carrier diluent.

9. The composition according to claim 8, wherein $R^1$ is hydrogen, $R^2$ is an alkoxy having 1 to 7 carbon atoms and $R^3$ is an alkyl having 1 to 4 carbon atoms.

10. The composition according to claim 8, wherein $R^1$ and $R^3$ are hydrogen and $R^2$ is an alkoxy having 1 to 7 carbon atoms.

11. The composition according to claim 8, wherein $R^1$ and $R^3$ are hydrogen and $R^2$ is 2-alkoxy having 1 to 7 carbon atoms.

12. The composition according to claim 8, wherein $R^1$ is hydrogen, $R^2$ is 2-alkoxy having 1 to 7 carbon atoms and $R^3$ is an alkali metal.

13. The composition according to claim 8, wherein the active compound is 1,6-dihydro-2-[2-(2-methylpropoxy)anilino]-6-oxo-5-pyrimidinecarboxylic acid.

14. The composition according to claim 8, wherein the active compound is sodium 1,6-dihydro-2-[2-(2-methylpropoxy)anilino]-6-oxo-5-pyrimidinecarboxylate.

* * * * *